(12) United States Patent
Cirakovic

(10) Patent No.: US 8,268,960 B2
(45) Date of Patent: Sep. 18, 2012

(54) PROCESS FOR THE SYNTHESIS OF 3-HYDROXYGLUTARONITRILE

(75) Inventor: Jelena Cirakovic, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 481 days.

(21) Appl. No.: 12/518,317

(22) PCT Filed: Dec. 11, 2007

(86) PCT No.: PCT/US2007/025298
§ 371 (c)(1),
(2), (4) Date: Jun. 9, 2009

(87) PCT Pub. No.: WO2008/073411
PCT Pub. Date: Jun. 19, 2008

(65) Prior Publication Data
US 2010/0029898 A1    Feb. 4, 2010

Related U.S. Application Data

(60) Provisional application No. 60/874,401, filed on Dec. 12, 2006.

(51) Int. Cl.
*C08G 73/06* (2006.01)
*C07C 253/30* (2006.01)
(52) U.S. Cl. ......... 528/422; 528/403; 528/482; 558/451
(58) Field of Classification Search .................. 528/422, 528/403, 482; 558/451
See application file for complete search history.

(56) References Cited

U.S. PATENT DOCUMENTS

| | | | |
|---|---|---|---|
| 2,816,879 A | 11/1951 | Wittbecker | |
| 3,554,966 A | 1/1971 | Jones et al. | |
| 3,943,125 A | 3/1976 | Gerber | |
| 4,110,412 A | 8/1978 | Danzig et al. | |
| 4,153,783 A | 5/1979 | Gagliani et al. | |
| 4,451,642 A | 5/1984 | Frazer et al. | |
| 4,736,015 A | 4/1988 | Rabilloud et al. | |
| 4,737,571 A | 4/1988 | Hodge et al. | |
| 5,061,784 A | 10/1991 | Mueller et al. | |
| 5,693,227 A | 12/1997 | Costa | |
| 5,939,553 A | 8/1999 | Reichwein et al. | |
| 5,965,753 A | 10/1999 | Masaki et al. | |
| 7,683,157 B2 | 3/2010 | Allen et al. | |
| 2006/0197053 A1 | 9/2006 | Shiflett et al. | |

FOREIGN PATENT DOCUMENTS

| | | |
|---|---|---|
| CA | 2355316 C | 10/2000 |
| EP | 0412359 B1 | 2/1991 |
| JP | 2002241357 A | 8/2002 |
| WO | 9711058 A1 | 3/1997 |
| WO | 9726254 A1 | 7/1997 |
| WO | 2006104974 A1 | 10/2006 |

OTHER PUBLICATIONS

Stamatov, S.D. et al., Regioselective Opening of an Oxirane System with Trifluoroacetic Anhydride. A General Method for the Synthesis of 2-Monoacyl- and 1,3-Symmetrical Triacylglycerols, Tetrahedron, vol. 61 (2005), pp. 3659-3669.
Nair, R.V. et al., Novel Synthesis and Enzymatic Resolution of (+/−)—2,3-Epoxy Propyl Esters, Synthetic Communications, vol. 29, No. 15 (1999), pp. 2559-2566.
Manaf, A. et al., Synthese De L'Epibromhydrine Avec Une Electromemranaire, Bull. Soc. Chim. FR, vol. 134 (1997) pp. 93-100. (Please See English Abstract, Document Was Only Available in French).
Kumar, G.S. et al., Chelating Copolymers Containing Photosensitive Functionalities, Macromolecules, vol. 17 (1984), pp. 2463-2467.
Kawakami et al., Reaction Modes of Fluorination of Cyclic Ethers by Potassium Fluoride-18-Crown-6, J. Org. Chem., vol. 45 (1980), pp. 3930-3932.
Johnson, F. et al., Polyfunctional Aliphatic Compounds. I. The Preparation of 3-Hydroxyglutaronitriles, J. Org. Chem, vol. 27 (1962), pp. 2241-2243.
Hay, M.R. et al., Palladium-Catalyzed Synthesis of Tetrahydrofurans From Gamma-Hydroxy Terminal Alkenes: Scope, Limitations and Stereoselectivity, J. Org. Chem, vol. 70 (2005), pp. 3099-3017.
Braun, G. et al., Oxidation of Unsaturated Compounds, II. Preparation and Configuration of the 3-Halogeno Derivatives of Crotonic Acid, J. Amer. Chem. Soc., vol. 52 (1930), pp. 3167-3176.
Berndt, T. et al., Catalyst-Free Gas-Phase Epoxidation of Alkenes, Chemistry Letters, vol. 34, No. 4 (2005), pp. 584-585.
Liu, D. et al., On Synthesis of Epilodohydrin, Harbin Ligong Daxue Xuebao, vol. 1, No. 3 (1996), English-Language Abstract Only.
Otera, J. et al., A Convenient Synthesis of Glycidyl Esters (2,3-Epoxy-Propyl Alkanoates), Synthesis, vol. 12 (1986), pp. 1019-1020.

*Primary Examiner* — Duc Truong
(74) *Attorney, Agent, or Firm* — Kevin S. Dobson

(57) ABSTRACT

A high yield and high productivity processes for preparing 3-hydroxyglutaronitrile by reacting an epihalohydrin or a 4-halo-3-hydroxy-butanenitrile, or analogous compound containing a different leaving group, with cyanide (CN—) in the presence of water and an ionic liquid. The use of an ionic liquid as a cosolvent with water results in increased productivity and selectivity.

10 Claims, No Drawings

PROCESS FOR THE SYNTHESIS OF 3-HYDROXYGLUTARONITRILE

This application claims the benefit of U.S. Provisional Application No. 60/874,401, filed 12 Dec. 2007, which is incorporated in its entirety as a part hereof for all purposes.

TECHNICAL FIELD

This invention relates to the manufacture of 3-hydroxyglutaronitrile, which is a useful intermediate in chemical synthesis.

BACKGROUND

The compound 3-hydroxyglutaronitrile ("3-HGN") is a precursor for a variety of useful materials, such as pharmaceutically active compounds, diamines used in hair coloring, and monomers for high-strength fibers. It has conventionally been synthesized by treating epichlorohydrin ("ECH") with an inorganic cyanide in water, producing 4-chloro-3-hydroxy-butanenitrile (also known as "chlorohydrin") as an intermediate, as shown for example by F. Johnson et al, *J. Org. Chem.* (1962), 27, 2241-2243):

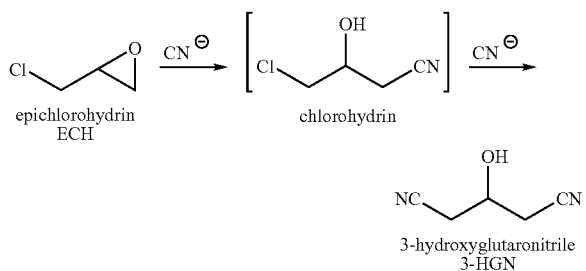

This process suffers from low productivity and byproduct formation. For example, Johnson et al reported 60% yield after about 54 hours reaction time at 10-11° C. and 48 hours of continual extraction with ethyl acetate. Significant byproducts (18%) included the intermediate 4-chloro-3-hydroxy-butanenitrile and 4-hydroxycrotononitrile.

A need thus remains for a process to synthesize 3-hydroxyglutaronitrile with increased productivity and selectivity.

SUMMARY

The inventions disclosed herein include processes for the preparation of 3-hydroxyglutaronitrile, processes for the preparation of products into which 3-hydroxyglutaronitrile can be converted, and the products obtained and obtainable by such processes.

This invention thus provides high yield and high productivity processes for preparing 3-hydroxyglutaronitrile by reacting an epihalohydrin or a 4-halo-3-hydroxy-butanenitrile, or a compound that is analogous to those starting materials, respectively, in which the leaving group is other than a halogen, with cyanide (CN—) in the presence of water and an ionic liquid. The use of an ionic liquid as a cosolvent with water results in increased productivity and selectivity.

One embodiment of the processes hereof provides a process for preparing 3-hydroxyglutaronitrile by (a) providing an aqueous solution of a CN— source; (b) adjusting the pH of the solution to about 8-10; (c) adding to the solution a compound as described generally by Formula (I):

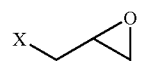

wherein X is a leaving group; (d) adding an ionic liquid and, optionally, a phase transfer catalyst to the solution; and (e) adding additional CN— continuously at a rate at which the pH of the solution is maintained at less than about 12, or discontinuously in more than one discrete portion.

Another embodiment of the processes hereof provides a process for preparing 3-hydroxyglutaronitrile by:
a. providing a biphasic mixture of water and an ionic liquid;
b. adding to the mixture a compound as described generally by Formula (II):

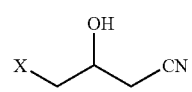

wherein X is a leaving group;
c. adding a CN— source and, optionally, a phase transfer catalyst to the mixture; and
d. adding additional CN— continuously at a rate at which the pH of the solution is maintained at less than about 12, or discontinuously in more than one discrete portion.

DETAILED DESCRIPTION

One embodiment of this invention provides a process for preparing 3-hydroxyglutaronitrile ("3-HGN") comprising the sequential steps:
a. providing an aqueous solution of a CN— source;
b. adjusting the pH of the solution to about 8 to about 10;
c. adding to the solution (i) an epihalohydrin (I):

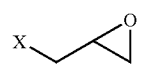

wherein X is a leaving group such as Cl, Br or I, or (ii) a compound that is analogous to the epihalohydrin in which X is a leaving group other than a halogen;
d. adding an ionic liquid, and optionally a phase transfer catalyst, to the solution;
e. adding additional CN— continuously at a rate at which the pH of the reaction mixture is maintained at less than about 12, or discontinuously in more than one discrete portion.

The 3-HGN product may, as desired, be isolated and recovered, or may be subjected directly to further steps to convert it to another product, such as another compound or a monomer, or an oligomer or a polymer formed therefrom.

The process is represented schematically below:

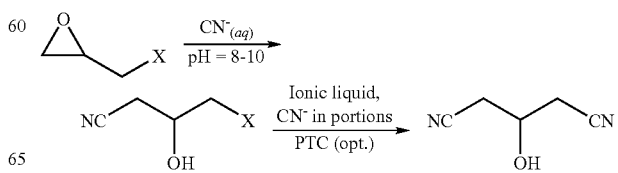

The use of an ionic liquid cosolvent increases process productivity by shortening the reaction time without a detrimental effect in yield. Cyanide is introduced continuously at a rate at which the pH of the reaction mixture is maintained at pH of less than about 12, or less than about 11, or in the range of about 9.5 to about 10.5; or discontinuously in more than one discrete portion. High pH degrades, or reduces the content in the reaction mixture of, the 3-hydroxy-butanenitrile intermediate. A convenient way to avoid high pH is to add the cyanide in portions. Other than avoiding a high pH, rigorous pH control during the reaction is thus not necessary when the cyanide is added in portions. Portions such as tenths, eighths or sixths have been found suitable, but the portions need not be equal in size. The intervals at which the various portions may be added may be an amount of time in the range of about 10 to about 80 minutes, or about 15 to about 60 minutes, or about 15 to about 30 minutes; but the intervals need not be equal length of time.

The aqueous solution provided in step (a) contains about 1 to about 1.5, preferably about 1.1 to about 1.3, moles of CN— for each mole of epihalohydrin (or analogous compound) that is to be added in step (c). Suitable CN— sources include without limitation alkali cyanides such as KCN, NaCN and LiCN; and trimethylsilyl cyanide. Acetone cyanohydrin may be used, in which case a base such as triethylamine is added with it in relative amounts such that more than one mole of acetone cyanohydrin is added per mole of base, or about 3 to about 4 moles of acetone cyanohydrin are added per mole of base.

The pH of the aqueous cyanide solution is then adjusted in step (b) by adding enough acid to lower the pH to the range of about 8 to about 10. A pH of about 8 is preferred. The specific acid used in step (b) is not critical; examples include but are not limited to $H_2SO_4$ and HCl.

In step (c), an epihalohydrin is added to the aqueous cyanide solution and allowed to react with the CN— source for a time sufficient to produce a 4-halo-3-hydroxy-butanenitrile [as described generally by Formula (II) when X is a halogen leaving group such as Cl, Br or I] as an intermediate, a sufficient time being, for example, about 10 to about 12 hours:

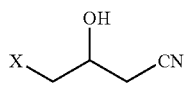

II

Alternatively, in step (c) a compound could be added that is analogous to an epihalohydrin, an analogous compound being one that has the same structure as an epihalohydrin, but has a leaving group that is not a halogen and is instead a group such as acetate, tosylate or mesylate. A leaving group in this context is a group that is readily displaced by the CN— ion. In such case, X in Formula I and Formula II will represent the alternative leaving group instead of the halogen, and references herein to epihalohydrin and to 4-halo-3-hydroxy-butanenitrile should be understood to include references to the relevant compounds created when X is a leaving group other than a halogen.

Epichlorohydrin is the preferred epihalohydrin and is readily available commercially. Epibromohydrin can be synthesized by epoxidation of pure or mixed dibromopropanol isomers [see, e.g., J. Manaf and R. Audinos, *Bull. Soc. Chim. Fr.* (1997) 134, 93-100; and G. Braun, *J. Amer. Chem. Soc.* (1930), 52, 3167-76]. Epibromohydrin (98% purity) is also commercially available from the Aldrich Chemical Company (Milwaukee, Wis., USA). Epiiodohydrin can be synthesized, for example, by reaction of epichlorohydrin with aqueous potassium iodide [D. Liu et al, *Harbin Ligong Daxue Xuebao* (1996), 1(3), 96-99]. Epiiodohydrin (X=I) and epibromohydrin (X=Br) can be synthesized by reaction of epichlorohydrin with KX in the presence of catalytic amounts of the crown ether 18-crown-6 [Y. Kawakami and Y. Yamashita, *J. Org. Chem.* (1980), 45(19), 3930-2].

Exemplary compounds with alternative leaving groups are also available in accordance with known processes. Suitable methods for preparing an acetoxy epoxide include those disclosed, for example, in the following sources:

Catalyst-free gas-phase epoxidation of alkenes; Berndt, Torsten and Boege, Olaf; Leibniz-Institut fuer Troposphaerenforschung e.V., Leipzig, Germany; Chemistry Letters (2005), 34(4), 584-585; Publisher: Chemical Society of Japan.

Regioselective opening of an oxirane system with trifluoroacetic anhydride, A general method for the synthesis of 2-monoacyl- and 1,3-symmetrical triacylglycerols; Stamatov, Stephan D. and Stawinski, Jacek; Department of Chemical Technology, University of Plovdiv, Plovdiv, Bulgaria; Tetrahedron (2005), 61(15), 3659-3669; Publisher: Elsevier B.V.

Novel synthesis and enzymatic resolution of (±)-2,3-epoxy propyl esters; Nair, Ranjeet V., Patil, Prashant N., and Salunkhe, Manikrao M.; Department of Chemistry, The Institute of Science, Mumbai, India; Synthetic Communications (1999), 29(15), 2559-2566; Publisher: Marcel Dekker, Inc.

Organotin templates in organic reactions; 7. A convenient synthesis of glycidyl esters (2,3-epoxypropyl alkanoates); Otera, Junzo and Matsuzaki, Shinjiro; Okayama Univ. Sci., Okayama, Japan; Synthesis (1986), (12), 1019-20.

Suitable methods for preparing an tosyloxy epoxide include those disclosed, for example, in the following sources:

Palladium-catalyzed synthesis of tetrahydrofurans from g-hydroxy terminal alkenes: Scope, limitations, and stereoselectivity; Hay, Michael B., Hardin, Alison R., and Wolfe, John P., Department of Chemistry, University of Michigan, Ann Arbor, Mich., USA; Journal of Organic Chemistry (2005), 70(8), 3099-3107; Publisher: American Chemical Society.

Poly(per)fluoroalkanesulfonyl fluoride-promoted olefin epoxidation with 30% aqueous hydrogen peroxide; Yan, Zhaohua and Tian, Weisheng; Shanghai Institute of Organic Chemistry, Laboratory of Organofluorine Chemistry, Chinese Academy of Sciences, Shanghai, Peop. Rep. China; Tetrahedron Letters (2004), 45(10), 2211-2213; Publisher: Elsevier Science B.V.

Process for producing glycidyl sulfonate derivatives by cyclization and sulfonation; Sakata, Midori, Furukawa, Yoshiro, Takenaka, and Keishi; Daiso Co., Ltd., Japan; WO 97/26254 A1 19970724.

Suitable methods for preparing a mesyloxy epoxide include those disclosed, for example, in Process and catalysts for the manufacture of epoxy sulfonates; Schroeder, Georg, Arlt, Dieter, and Jautelat, Manfred; Bayer A.-G., Germany; EP 412,359 A1 19910213.

A suitable temperature of the aqueous solution in steps (a), (b) and (c) may be, for example, in the range of about 0 to about 25° C. For step (d), if the solution is not already at ambient temperature prior to step (d), it is typically allowed to come to ambient temperature; alternatively, it may be brought to temperature by gentle heating. Temperatures higher than about 25° C. may result in faster reaction but lower yield of 3-HGN.

In step (d), an ionic liquid cosolvent or a mixture of ionic liquids, and optionally a phase transfer catalyst ("PTC"), are added at ambient temperature, and the resulting mixture is heated for an additional time period. Heating to about 40 to about 65° C. for a period of up to about 1 hour has been found suitable.

An ionic liquid is a liquid composed entirely of ions that is fluid at about or below 100° C., as more particularly described in Science (2003) 302:792-793. Ionic liquids are typically organic salts. In the process of this invention, it is preferred but not required that the ionic liquid not be soluble in water. Examples of suitable ionic liquids include without limitation 1-butyl-3-methylimidazolium hexafluorophosphate ("[BMIM]PF$_6$"), 1-butyl-3-methylimidazolium 2-H-perfluoropropane sulfonate, 1-butyl-3-methylimidazolium tetrafluoroborate ("[BMIM]BF$_4$"), 1-ethyl-3-methylimidazolium 1,1,2-trifluoro-2-(pentafluoroethoxy)-ethanesulfonate, and 1-hexyl-3-methylimidazolium hexafluorophosphate. [BMIM]PF$_6$ is preferred. Other ionic liquids suitable for use herein are disclosed in U.S. 2006/0197053, which is incorporated in its entirety as a part hereof for all purposes, and in the references cited therein. The volume of ionic liquid added is about the same as the volume of water in step (a).

A phase transfer catalyst suitable for use herein includes one or more members of a class of known substances that enhances the rate of reaction between chemical species located in different phases (for example, immiscible liquids) by extracting one of the reactants, most commonly an anion, across the interface into the other phase so that reaction can proceed. Phase transfer catalysts are typically salts of "onium ions" (for example, tetraalkylammonium salts) or agents that can complex inorganic cations (for example, crown ethers). Examples of suitable phase transfer catalysts include without limitation tetraalkylammonium salts such as tetrabutylammonium iodide ("TBAI") and specific crown ethers as indicated by the size of the cation if the CN— source is an alkali cyanide (for example, 18-crown-6 for K+ when KCN is the cyanide source). TBAI is preferred. In the absence of a phase transfer catalyst, 3-HGN may be produced in lower yield; thus, use of a phase transfer catalyst is optional but preferred. When used, the amount of phase transfer catalyst is about 0.01 to about 0.10 mol, preferably about 0.05 to 0.1 mol, per mol of epihalohydrin.

In step (e), CN— is typically added such that the total amount of CN— added in steps (a) and (e) combined is at least about 2.05 moles of CN— per mole of epihalohydrin added in step (c). For example, if the aqueous solution in step (a) is made with about 1.25 moles of CN— and in step (c) about 1 mole of epihalohydrin is added, then at least an additional 0.80 moles of CN— will typically be added in step (e). Cyanide is also introduced continuously at a rate at which the pH of the reaction mixture is maintained at pH of less than about 12, or less than about 11, or in the range of about 9.5 to about 10.5; or discontinuously in more than one discrete potion. A convenient way to avoid high pH is to add the cyanide in portions. Other than avoiding a high pH, rigorous pH control during the reaction is thus not necessary when the cyanide is added in portions. Portions such as tenths, eighths or sixths have been found suitable, but the portions need not be equal in size. The intervals at which portions may be added may be an amount of time in the range of about 10 to about 80 minutes, or about 15 to about 60 minutes, or about 15 to about 30 minutes; but the intervals need not be equal in length of time. In the case mentioned above, for example, the 0.80 moles could be divided into, e.g., 8 portions, each containing 0.10 mole CN—, and one portion could be added every 15 to 30 minutes until all 8 portions had been added.

After the last addition of CN—, the mixture is stirred with heating for an additional time period. Temperatures in the range of about 45 to about 65° C. for a period of about 45 min to about 2 h have been found suitable. The reaction mixture is then cooled to allow the organic and aqueous layers to separate. In general, the 3-HGN product resides largely in the aqueous phase, and the water layer may thus be extracted with, for example, ethyl acetate, tetrahydrofuran ("THF"), cyclopentanone, cyclohexanone, or methylethylketone ("MEK"). The organic extracts are concentrated, and the residue is purified by any suitable means known in the art (for example, column chromatography) to yield the product 3-HGN as a yellow oil.

The 3-HGN product may, as desired, be isolated and recovered, or may be subjected directly to further steps to convert it to another product, such as another compound or an oligomer or a polymer.

A second embodiment of this invention provides a process for preparing 3-hydroxyglutaronitrile comprising the sequential steps:

a. providing a biphasic mixture of water and an ionic liquid;
b. adding to the mixture (i) a 4-halo-3-hydroxy-butanenitrile:

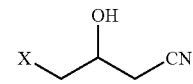

wherein X is a leaving group such as Cl, Br or I, or (ii) a compound that is analogous to the 4-halo-3-hydroxy-butanenitrile in which X is a leaving group other than a halogen;

c. adding a CN— source, and optionally a phase transfer catalyst, to the mixture; and d. adding additional CN— continuously at a rate at which the pH of the reaction mixture is maintained at less than about 12, or discontinuously in more than one discrete portion.

As discussed above, ionic liquids that are not soluble in water are preferred, but not required, for use in step (a). [BMIM]PF$_6$ is a suitable choice as the ionic liquid. The volume of ionic liquid in the biphasic mixture is about the same as the volume of water.

A 4-halo-3-hydroxy-butanenitrile (II) for addition in step (b) can be produced by reacting the corresponding epoxide with LiX (X=Cl, Br or I) as described in Bajwa et al, Tetrahedron Letters (1991), 32(26), 3021-4; or with HCN in the presence of a sulfate, nitrate and/or phosphate of an alkali metal or alkaline earth metal in water as described in JP 2002/241,357. 4-chloro-3-hydroxybutanenitrile is preferred and is commercially available.

Alternatively, in step (b) a compound could be added that is analogous to a 4-halo-3-hydroxy-butanenitrile, an analogous compound being one that has the same structure as a 4-halo-3-hydroxy-butanenitrile, but has a leaving group that is not a halogen and is instead a group such as acetate, tosylate or mesylate. A leaving group in this context is a group that is readily displaced by the CN— ion. In such case, X in Formula II will represent the alternative leaving group instead of the halogen, and references herein to 4-halo-3-hydroxy-butanenitrile should be understood to include references to the relevant compounds created when X is a leaving group other than a halogen.

A suitable CN— source, and the optional phase transfer catalyst, for addition in step (c) are as described above. KCN is preferred, and the use of TBAI as a phase transfer catalyst is preferred. The mixture produced in step (c) is heated, and heating to a temperature in the range of about 40 to about 65° C. has been found suitable for this purpose.

In step (d), CN— is added in an amount such that the total amount of CN— added in steps (c) and (d) combined is at least about 2.05 moles of CN— per mole of 4-halo-3-hydroxy-butanenitrile (or analogous compound with a non-halogen leaving group) added in step (b). Cyanide is introduced continuously at a rate at which the pH of the reaction mixture is maintained at pH of less than about 12, or less than about 11, or in the range of about 9.5 to about 10.5; or discontinuously in more than one discrete portion. Portions such as tenths, eighths or sixths have been found suitable, but the portions need not be equal in size. The intervals at which portions may be added may be an amount of time in the range of about 10 to about 80 minutes, or about 15 to about 60 minutes, or about 15 to about 30 minutes; but the intervals need not be equal in length of time.

After the last addition of CN—, the mixture is stirred with heating for an additional time period. Temperatures in the range of about 45 to about 65° C. for a period of about 45 min to about 2 h have been found suitable. The reaction mixture is then cooled to allow the organic and aqueous layers to separate. In general, the 3-HGN product resides largely in the aqueous phase, and the water layer may thus be extracted with, for example, ethyl acetate, tetrahydrofuran ("THF"), cyclopentanone, cyclohexanone, or methylethylketone ("MEK"). The organic extracts are concentrated, and the residue is purified by any suitable means known in the art (for example, column chromatography) to yield the product 3-HGN as a yellow oil.

The 3-HGN product may, as desired, be isolated and recovered as described above. It may also be subjected with or without recovery from the reaction mixture to further steps to convert it to another product such as another compound (e.g. a monomer), or an oligomer or a polymer. Another embodiment of a process hereof thus provides a process for converting 3-HGN, through one or more reactions, into another compound, or into an oligomer or a polymer. 3-HGN may be made by a process such as described above, and then converted, for example, into a compound such as a diaminopyridine. In a multi-step process, a diaminopyridine may in turn be subjected to a polymerization reaction to prepare an oligomer or polymer therefrom, such as those having amide functionality, imide functionality, or urea functionality, or a pyridobisimidazole-2,6-diyl(2,5-dihydroxy-p-phenylene) polymer.

3-HGN may be converted into a diaminopyridine by a process in which 3-HGN is reacted with ammonia or an ammonium donor such as an aliphatic, cyclic or aromatic amine, including amines such as n-butylamine, benzylamine, piperazine and aniline. The reaction is carried out in a solvent such as an alcohol at a temperature of 100-200° C., with the preferable use of a transition metal catalyst such as copper, cobalt, manganese or zinc salt. A process similar to the foregoing is described in U.S. Pat. No. 5,939,553.

A diaminopyridine (and thus ultimately 3-HGN as its precursor) may be converted into a polyamide oligomer or polymer by reaction with a diacid (or diacid halide) in a process in which, for example, the polymerization takes place in solution in an organic compound that is liquid under the conditions of the reaction, is a solvent for both the diacid(halide) and the diaminopyridine, and has a swelling or partial salvation action on the polymeric product. The reaction may be effected at moderate temperatures, e.g. under 100° C., and is preferably effected in the presence of an acid acceptor that is also soluble in the chosen solvent. Suitable solvents include methyl ethyl ketone, acetonitrile, N,N-dimethylacetamide dimethyl formamide containing 5% lithium chloride, and N-methyl pyrrolidone containing a quaternary ammonium chloride such as methyl tri-n-butyl ammonium chloride or methyl-tri-n-propyl ammonium chloride. Combination of the reactant components causes generation of considerable heat and the agitation, also, results in generation of heat energy. For that reason, the solvent system and other materials are cooled at all times during the process when cooling is necessary to maintain the desired temperature. Processes similar to the foregoing are described in U.S. Pat. No. 3,554,966; U.S. Pat. No. 4,737,571; and CA 2,355,316.

A diaminopyridine (and thus ultimately 3-HGN as its precursor) may also be converted into a polyamide oligomer or polymer by reaction with a diacid (or diacid halide) in a process in which, for example, a solution of the diaminopyridine in a solvent may be contacted in the presence of an acid acceptor with a solution of a diacid or diacid halide, such as a diacid chloride, in a second solvent that is immiscible with the first to effect polymerization at the interface of the two phases. The diaminopyridine may, for example, be dissolved or dispersed in a water containing base with the base being used in sufficient quantities to neutralize the acid generated during polymerization. Sodium hydroxide may be used as the acid acceptor. Preferred solvents for the diacid(halide) are tetrachloroethylene, methylenechloride, naphtha and chloroform. The solvent for the diacid(halide) should be a relative non-solvent for the amide reaction product, and be relatively immiscible in the amine solvent. A preferred threshold of immiscibility is as follows: an organic solvent should be soluble in the amine solvent not more than between 0.01 weight percent and 1.0 weight percent. The diaminopyridine, base and water are added together and vigorously stirred. High shearing action of the stirrer is important. The solution of acid chloride is added to the aqueous slurry. Contacting is generally carried out at from 0° C. to 60° C., for example, for from about 1 second to 10 minutes, and preferably from 5 seconds to 5 minutes at room temperature. Polymerization occurs rapidly. Processes similar to the foregoing are described in U.S. Pat. No. 3,554,966 and U.S. Pat. No. 5,693,227.

A diaminopyridine (and thus ultimately 3-HGN as its precursor) may also be converted into a polyimide oligomer or polymer by reaction with a tetraacid (or halide derivative thereof) or a dianhydride in a process in which each reagent (typically in equimolar amounts) is dissolved in a common solvent, and the mixture is heated to a temperature in the range of 100~250° C. until the product has a viscosity in the range of 0.1~2 dL/g. Suitable acids or anhydrides include benzhydrol 3,3',4,4'-tetracarboxylic acid, 1,4-bis(2,3-dicarboxyphenoxy)benzene dianhydride, and 3,3',4,4'-benzophenone tetracarboxylic acid dianhydride. Suitable solvents include cresol, xylenol, diethyleneglycol diether, gamma-butyrolactone and tetramethylenesulfone. Alternatively, a polyamide-acid product may be recovered from the reaction mixture and advanced to a polyimide by heating with a dehydrating agent such as a mixture of acetic anhydride and beta picoline. Processes similar to the foregoing are described in U.S. Pat. No. 4,153,783; U.S. Pat. No. 4,736,015; and U.S. Pat. No. 5,061,784.

A diaminopyridine (and thus ultimately 3-HGN as its precursor) may also be converted into a polyurea oligomer or polymer by reaction with a polyisocyanate, representative examples of which include toluene diisocyanate; methylene bis(phenyl isocyanates); hexamethylene diisocycanates; phenylene diisocyanates. The reaction may be run in solution, such as by dissolving both reagents in a mixture of tetramethylene sulfone and chloroform with vigorous stirring at ambient temperature. The product can be worked up by separation with water, or acetone and water, and then dried in a vacuum oven. Processes similar to the foregoing are described in U.S. Pat. No. 4,451,642 and Kumar, Macromolecules 17, 2463 (1984). The polyurea forming reaction may also be run under interfacial conditions, such as by dissolving the diaminopyridine in an aqueous liquid, usually with an acid acceptor or a buffer. The polyisocyanate is dissolved in an organic liquid such as benzene, toluene or cyclohexane. The polymer product forms at the interface of the two phases upon vigorous stirring. Processes similar to the foregoing are described in U.S. Pat. No. 4,110,412 and Millich and Carraher, Interfacial Syntheses Vol. 2, Dekker, New York, 1977. A diaminopyridine may also be converted into a polyurea by reaction with phosgene, such as in an interfacial process as described in U.S. Pat. No. 2,816,879.

A diaminopyridine (and thus ultimately 3-HGN as its precursor) may also be converted into a pyridobisimidazole-2,6-diyl(2,5-dihydroxy-p-phenylene) polymer by (i) converting the diaminopyridine to a diamino dinitropyridine, (ii) converting the diamino dinitropyridine to a tetramino pyridine, and (iii) converting the tetramino pyridine to a pyridobisimidazole-2,6-diyl(2,5-dihydroxy-p-phenylene) polymer.

A diaminopyridine (and thus ultimately 3-HGN as its precursor) may be converted to a diamino dinitropyridine by contacting it with nitric acid and a solution of sulfur trioxide in oleum, as discussed in WO 97/11058. A diamino dinitropyridine may be converted to a tetramino pyridine by hydrogenation using a hydrogenation catalyst in the presence of a strong acid, and using a cosolvent such as a lower alcohol, an alkoxyalcohol, acetic acid or propionic acid, as discussed in U.S. Pat. No. 3,943,125.

A tetramino pyridine (and thus ultimately 3-HGN as its precursor) may be converted to a pyridobisimidazole-2,6-diyl (2,5-dihydroxy-p-phenylene) polymer by polymerizing a 2,5-dihydroxyterephthalic acid with the trihydrochloride-monohydrate of tetraminopyridine in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application No. 60/665, 737, filed Mar. 28, 2005 (which is incorporated in its entirety as a part hereof for all purposes), published as WO 2006/104974. The pyridobisimidazole-2,6-diyl(2,5-dihydroxy-p-phenylene) polymer so produced may be, for example, a poly(1,4-(2,5-dihydroxy)phenylene-2,6-pyrido[2,3-d:5,6-d'] bisimidazole) polymer, or a poly[(1,4-dihydrodiimidazo[4,5-b:4',5'-e]pyridine-2,6-diyl)(2,5-dihydroxy-1,4-phenylene)] polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replaced by the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

The advantageous attributes and effects of the processes hereof may be seen in a series of examples (Examples 1-7), as described below. The embodiments of these processes on which these examples are based are illustrative only, and the selection of those embodiments to illustrate the invention does not indicate that conditions, arrangements, approaches, regimes, techniques, protocols and reactants not described in these examples are not suitable for practicing these processes, or that subject matter not described in these examples is excluded from the scope of the appended claims and equivalents thereof. The significance of the examples is better understood by comparing the results obtained therefrom with the results obtained from a reaction that was designed to serve as a controlled experiment (Control A) and provide a basis for such comparison since an ionic liquid was not used during the reaction.

The following materials were used in the examples. All commercial reagents were used as received.

Tetrabutylammonium iodide (98% purity), acetone cyanohydrin (99% purity), triethyl amine (99.5% purity) and epichlorohydrin (99% purity) were obtained from the Aldrich Chemical Company (Milwaukee, Wis., USA).

Potassium cyanide (97% purity) was obtained from Sigma-Aldrich (St. Louis, Mo., USA).

1-butyl-3-methylimidazolium hexafluorophosphate (purity not specified) and 1-hexyl-3-methylimidazolium hexafluorophosphate (purity not specified) were obtained from Acros Organic (Geel, Belgium).

4-chloro-3-hydroxybutanenitrile was synthesized from epichlorohydrin and one equivalent of cyanide as follows: Sodium cyanide (9.93 g) was dissolved in 60 mL of water, and the solution was cooled to 0° C. To this solution was added concentrated sulfuric acid, dropwise, until the pH of the solution was 8.5. Epichlorohydrin (15 g) was then added dropwise, and the mixture was allowed to reach room temperature overnight. The reaction mixture was then extracted three times with ethyl acetate, dried over sodium sulfate, filtered and concentrated in vacuo. 18.5 g (96% isolated yield) of 4-chloro-3-hydroxybutanenitrile was obtained. The purity was at least 95%, the limit of the NMR measurement.

1-Butyl-3-methylimidazolium 2-H-perfluoropropane sulfonate was synthesized by reacting 1-butyl-3-methylimidazolium chloride with potassium-1,1,2,3,3,3-hexafluoropropanesulfonate in acetone as described in Example 10 of U.S. Provisional Patent Application 60/719,370, which is incorporated in its entirety as a part hereof for all purposes. Similarly, 1-ethyl-3-methylimidazolium 1,1,2-trifluoro-2-(pentafluoroethoxy)-ethanesulfonate was synthesized by reacting 1-ethyl-3-methylimidazolium chloride with potassium 1,1,2-trifluoro-2-(perfluoroethoxy)ethanesulfonate in acetone according to the methods described also in U.S. Provisional Patent Application 60/719,370.

The meaning of abbreviations is as follows: "TBAI" means tetrabutylammonium iodide, "THF" means tetrahydrofuran, "EtOAc" means ethyl acetate, "h" means hour(s), "min" means minute(s), "mL" means milliliter(s), "g" means gram(s), "mmol" means millimole(s), and "NMR" means nuclear magnetic resonance spectroscopy. The term "brine" as used herein denotes a saturated solution of sodium chloride in water.

Example 1

To a solution of potassium cyanide (0.224 g, 3.587 mmol) in water (7.00 mL) was added concentrated $H_2SO_4$ until pH of the solution reached 8. The solution was then cooled in an ice bath, and epichlorohydrin was then added dropwise (0.22 mL, 0.281 mmol). Five minutes later, the bath was removed, and the mixture was allowed to reach room temperature over 12 h. 1-butyl-3-methylimidazolium hexafluorophosphate (6.00 mL) was then added, followed by tetrabutylammonium iodide (0.097 g, 0.262 mmol). The biphasic mixture was heated to 45° C. for one hour. After that time, potassium cyanide was added in eight portions, 0.016 g (0.248 mmol) each, one portion every 30 minutes. After the final cyanide addition, the reaction mixture was heated to 65° C. for two hours. The mixture was then cooled to room temperature and the layers were separated. The ionic liquid layer was extracted with brine (3.0 mL) once. Mixed aqueous layers were extracted with THF (4 portions, 5 mL each). The combined organic extracts were dried over $Na_2SO_4$ and concentrated in vacuo. Purification by column chromatography (hexanes: EtOAc=3:2 to hexanes: EtOAc=1:1 produced pure 3-hydroxyglutaronitrile (0.247 g, 80% isolated yield).

Example 2

To a cooled (0° C.) solution of KCN (2.04 g, 31.3 mmol) in water was added sulfuric acid until the pH of the solution was 8. Epichlorohydrin (2.31 g, 25.0 mmol) was then added and the mixture allowed to reach room temperature over 11 h. Tetrabutylammonium iodide (0.920 g, 2.5 mmol) and ionic liquid [BMIM]$PF_6$ (10.0 mL) were then added to the reaction mixture, and the resulting biphasic mixture was heated to 45° C. After one hour, KCN was added in 8 portions of 0.130 g (20 mmol) each, one portion every 30 min. After the final cyanide addition, the mixture was left stirring at 45° C. for 45 min. The mixture was then cooled to room temperature, and the layers were separated. The water layer was extracted with ethyl acetate. Organic extracts were concentrated, and the residue was purified by column chromatography to yield 3-HGN as a yellow oil (80% isolated yield)

Example 3

To a biphasic mixture of water (2.00 mL) and 1-butyl-3-methylimidazolium hexafluorophosphate (2.00 mL) was added 4-chloro-3-hydroxybutanenitrile (0.079 g, 0.660 mmol), followed by TBAI (0.025 g, 0.067 mmol), and potassium cyanide (0.007 g, 0.104 mmol). The mixture was heated to 45° C. Every 30 min, potassium cyanide (~0.004 g, 0.061 mmol) was added, with a total amount of potassium cyanide being 0.046 g (0.706 mmol). The mixture was then heated to 65° C. for two hours. The mixture was then cooled to room temperature and the layers were separated. The water layer was diluted with brine (5.0 mL) and was then extracted with THF (3 portions, 5 mL each). The organics were then dried over $Na_2SO_4$ and concentrated. Purification by column chromatography (hexanes: EtOAc=1:1) produced pure 3-HGN (0.060 g, 82% isolated yield).

Example 4

To a biphasic mixture of water (4.00 mL) and 1-butyl-3-methylimidazolium 2-H-perfluoropropane sulfonate (4.00 mL) was added 4-chloro-3-hydroxy-butanenitrile (0.109 g, 0.912 mmol), followed by TBAI (0.047 g, 0.126 mmol), and potassium cyanide (0.007 g, 0.104 mmol). The mixture was heated to 45° C. Every 30 min, potassium cyanide (~0.006 g, 0.096 mmol) was added, with a total amount of potassium cyanide being 0.062 g (0.957 mmol). The mixture was then heated to 65° C. for two hours. The mixture was then cooled to room temperature and the layers were separated. The water layer was diluted with brine (5.0 mL) and was then extracted with THF (3 portions, 5 mL each). The organics were then dried over $Na_2SO_4$ and concentrated. Purification by column chromatography (hexanes: EtOAc=1:1) produced pure 3-HGN (0.045 g, 47% isolated yield).

Example 5

To a biphasic mixture of water (3.00 mL) and 1-ethyl-3-methylimidazolium 1,1,2-trifluoro-2-(pentafluoroethoxy)-ethanesulfonate (3.00 mL) was added 4-chloro-3-hydroxy-butanenitrile (0.299 g, 2.500 mmol), followed by TBAI (0.090 g, 0.250 mmol), and potassium cyanide (0.018 g, 0.275 mmol). The mixture was heated to 45° C. Every 30 min, potassium cyanide (~0.018 g, 0.275 mmol) was added, with a total amount of potassium cyanide being 0.180 g (2.750 mmol). The mixture was then heated to 65° C. for two hours. The mixture was then cooled to room temperature and the layers were separated. The water layer was diluted with brine (5.0 mL) and was then extracted with THF (3 portions, 5 mL each). The organics were then dried over $Na_2SO_4$ and concentrated. Purification by column chromatography (hexanes: EtOAc=1:1) produced pure 3-HGN (0.220 g, 80% isolated yield).

Example 6

To a biphasic mixture of water (3.00 mL) and 1-hexyl-3-methylimidazolium hexafluorophosphate (3.00 mL) was added 4-chloro-3-hydroxy-butanenitrile (0.299 g, 2.500 mmol), followed by TBAI (0.090 g, 0.250 mmol), and potassium cyanide (0.018 g, 0.275 mmol). The mixture was heated to 45° C. Every 30 min, potassium cyanide (~0.018 g, 0.275 mmol) was added, with a total amount of potassium cyanide being 0.180 g (2.750 mmol). The mixture was then heated to 65° C. for two hours. The mixture was then cooled to room temperature and the layers were separated. The water layer was diluted with brine (5.0 mL) and was then extracted with THF (3 portions, 5 mL each). The organics were then dried over $Na_2SO_4$ and concentrated. Purification by column chromatography (hexanes: EtOAc=1:1) produced pure 3-HGN (0.228 g, 81% isolated yield).

Example 7

To a flask containing water (1.50 mL) and 1-methyl-3-butylimidazolium hexafluorophosphate (1.50 mL) were added 3-hydroxy-4-chlorobutanenitrile (0.359 g, 3.000 mmol) and tetrabutylammonium iodide (0.111 g, 0.300 mmol). The biphasic mixture was stirred and triethylamine (0.042 mL, 0.300 mmol) and acetone cyanohydrin (0.091 mL, 0.990 mmol) were added. The mixture was warmed to 45° C. Every 30 min, one portion of about 0.042 mL (0.300 mmol) triethylamine and about 0.091 mL (0.990 mmol) acetone cyanohydrin was added to the reaction mixture until nine such portions had been added, so that with the total amount of triethylamine added was 0.418 mL (3.000 mmol), and the total amount of acetone cyanohydrin added was 0.906 mL (9.900 mmol). The mixture was then heated to 65° C. for one hour. Thin layer chromatography analysis of the reaction mixture revealed ~50% of it was the desired product, 3-HGN.

Control A

To a biphasic mixture of water (1.00 mL) and ethyl acetate (1.00 mL) was added 4-chloro-3-hydroxy-butanenitrile (0.177 g, 1.481 mmol), TBAI (0.054 g, 0.145 mmol), and potassium cyanide (0.011 g, 0.170 mmol), and the mixture was heated to 65° C. Every 30 min, potassium cyanide (~0.011 g, 0.170 mmol) was added, with a total amount of potassium cyanide being 0.110 g (1.700 mmol). The mixture was cooled after the addition and the layers were separated.

The water layer was extracted with ethyl acetate ten times. Combined organic extracts were washed with saturated aqueous NH$_4$Cl and brine, dried over Na$_2$SO$_4$ and dried in vacuo. NMR analysis of the residue revealed 0.057 g of 3-hydroxyglutarinitrile (35% isolated yield).

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited.

Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

What is claimed is:

1. A process for preparing 3-hydroxyglutaronitrile comprising the steps of (a) providing an aqueous solution of a CN$^-$ source; (b) adjusting the pH of the solution to about 8-10; (c) adding to the solution a compound as described generally by Formula(I):

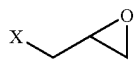

wherein X is a leaving group; (d) adding an ionic liquid, wherein the ionic liquid is a composition composed entirely of ions, and wherein the composition is fluid below about 100° C., and, optionally, a phase transfer catalyst to the solution; and (e) adding additional CN— continuously at a rate at which the pH of the solution is maintained at less than about 12, or discontinuously in more than one discrete portion.

2. The process of claim 1 wherein the CN— source comprises an alkali cyanide, trimethylsilyl cyanide or acetone cyanohydrin.

3. The process of claim 1 wherein X is selected from the group consisting of Cl, Br, I, acetate, tosylate and mesylate.

4. The process of claim 1 wherein the ionic liquid is selected from the group consisting of 1-butyl-3-methylimidazolium hexafluorophosphate, 1-butyl-3-methylimidazolium 2-H-perfluoropropane sulfonate, 1-butyl-3-methylimidazolium tetrafluoroborate, 1-ethyl-3-methylimidazolium 1,1,2-trifluoro-2-(pentafluoroethoxy)-ethanesulfonate, and 1-hexyl-3-methylimidazolium hexafluorophosphate.

5. The process of claim 1 wherein the solution comprises a phase transfer catalyst.

6. The process of claim 1 wherein, in step (e), the additional CN— is added in 8 to 10 portions.

7. The process of claim 1 wherein one portion of CN— is added every 15 to 30 minutes.

8. The process of claim 1 wherein 3-hydroxyglutaronitrile is subjected, without recovery from the reaction mixture, to conversion to a compound, monomer, oligomer or polymer.

9. A process according to claim 1 further comprising a step of subjecting the 3-hydroxyglutaronitrile to a reaction to prepare therefrom a compound, monomer, oligomer or polymer.

10. A process according to claim 9 wherein a polymer prepared comprises a pyridobisimidazole-2,6-diyl(2,5-dihydroxy-p-phenylene) polymer, or a poly[(1,4-dihydrodiimidazo[4,5-b:4 ',5'-e]pyridine-2,6-diyl) (2,5-dihydroxy-1,4-phenylene)] polymer.

* * * * *